United States Patent [19]

Eckstein et al.

[11] Patent Number: 5,847,152
[45] Date of Patent: Dec. 8, 1998

[54] PREPARATION OF A D-(+)-BIOTIN INTERMEDIATE

[75] Inventors: Jürgen Eckstein, Rossdorf; Thomas Koppe, Darmstadt; Michael Schwarz, Gross-Gerau; Michael Casutt, Heppenheim, all of Germany

[73] Assignee: Merck Patent Gesellschaft mit beschrankter Haftung, Germany

[21] Appl. No.: 702,450

[22] PCT Filed: Feb. 18, 1995

[86] PCT No.: PCT/EP95/00593

§ 371 Date: Sep. 26, 1996

§ 102(e) Date: Sep. 26, 1996

[87] PCT Pub. No.: WO95/26965

PCT Pub. Date: Oct. 12, 1995

[30] Foreign Application Priority Data

Mar. 30, 1994 [DE] Germany .......................... 44 11 101.0

[51] Int. Cl.⁶ .................................................. C07D 495/04
[52] U.S. Cl. ..................................... 548/303.7; 548/303.1
[58] Field of Search ............................................ 548/303.7

[56] References Cited

U.S. PATENT DOCUMENTS 5,235,065   8/1993   Schwarz et al. ..................... 548/303.7

FOREIGN PATENT DOCUMENTS 0273270  10/1987  European Pat. Off. .

OTHER PUBLICATIONS

Chem. Abst., Ichiro et al. vol. 70, 1969; p. 1990, 19984 r.

Primary Examiner—Mukund J. Shah
Assistant Examiner—Pavanaram K. Sripada
Attorney, Agent, or Firm—Millen, White, Zelano & Branigan, P.C.

[57] ABSTRACT

The present invention relates to an improved process for making heterocyclic compounds suitable for intermediate products for making D-(+)-biotin and a process for making D-(+)-biotin itself.

14 Claims, No Drawings

PREPARATION OF A D-(+)-BIOTIN INTERMEDIATE

This application is a 371 of PCT/EP95/00593 Feb. 18, 1995.

The present invention relates to an improved process for the preparation of heterocyclic compounds which are suitable as intermediates for the preparation of D-(+)-biotin, and to a process for the preparation of D-(+)-biotin itself.

D-(+)-biotin is a substance which has been known for a long time, and accordingly there are also already a number of processes known for its preparation. Common to the processes of industrial interest is the necessity at some particular stage of attaching the carboxybutyl side chain to the ring system. Various solutions for this have been disclosed, such as, for example, the synthesis of the side chain according to the linkage scheme $C_4+C_1 \rightarrow C_5$ or alternatively $C_3+(C_3-C_1=C_2) \rightarrow C_5$ (e.g. CH Patent Specification 556 867).

It is also known to link the side chain to the ring system in one step by means of a Wittig reaction (e.g. EP Offenlegungsschrift 0 084 337). All these processes, however, have the disadvantage that they either proceed via a comparatively large number of reaction steps or else require a relatively large outlay for the isolation of the desired final product.

Furthermore, EP Offenlegungsschrift 0 154 225 discloses the introduction of the side chain by reaction of the thiolactone of the formula I with 4-(2,4,10-tri-oxaadamantyl) butylmagnesium bromide.

In addition, the introduction of the carboxybutyl side chain via a "bis-Grignard reaction" using a 1,4-dihalomagnesium butane and subsequent carboxylation with carbon dioxide has been known for a long time. According to JP-B-003,580/71 and DE Offenlegungsschrift 20 58 234, the reaction is carried out in a solvent mixture of diethyl ether and toluene.

On the other hand, JP-A-280,037/84 and EP-A-0 273 270 propose carrying out the reaction in tetrahydrofuran in the presence of tetramethylethylenediamine (TMEDA).

In all these cases, the addition product of the formula III

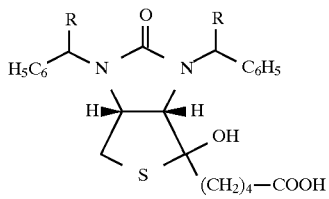

is first isolated, at least as a crude extract, and then dehydrated.

These processes, however, have various disadvantages, which can appear to make them unsuitable for industrial implementation.

Only according to the process described in JP-A-280,037/84 can the D-(+)-biotin intermediate of the formula I be prepared in very good yield.

However, this requires the use of the cosolvent TMEDA, which is classified as irritant, as a result of which the working up of the reaction mixture becomes particularly laborious, as this cosolvent must not pass into the effluent.

In addition, the process described there is carried out at high dilution, and the carrying-out of the carboxylation at temperatures between $-40°$ and $-45°$ C. can only be realized with difficulty on the industrial scale.

Furthermore, the dehydration of the Grignard adduct of the formula III is carried out in a solvent mixture of toluene/tetrahydrofuran, which, after working up, must be separated for recycling in a complicated process.

The object of the present invention was then to indicate a process in which the D-(+)-biotin intermediate of the formula I can be prepared in THF as solvent without the use of the cosolvent TMEDA in an improved space-time yield.

There was thus a need for an industrially simple process according to which the side chain can be attached to the ring system in good yield, and, as far as possible, in a "one-pot process". This is now possible by means of the process according to the invention.

The invention thus relates to an improved process for the preparation of a D-(+)-biotin intermediate of the formula I

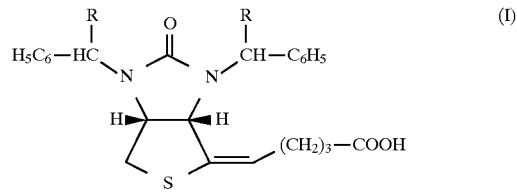

in which
R is H or $C_{1-6}$-alkyl,
by reacting the thiolactone of the formula II

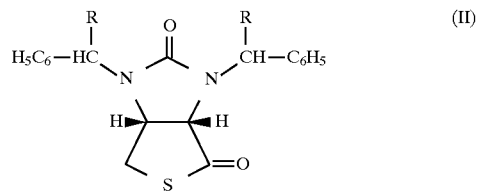

in which R has the meaning. indicated, with 1,4-dimagnesiumchlorobutane and carbon dioxide in an inert solvent and subsequent elimination of water using a mineral acid, characterized in that the following steps are carried out successively:

a) reaction of 1,4-dichlorobutane with magnesium turnings in the presence of catalytic amounts of 1,2-dibromoethane in tetrahydrofuran as a solvent, b) adding the thiolactone of the formula II, dissolved in tetrahydrofuran at temperatures between $-25°$ and $-15°$ C., and, if appropriate, subsequent stirring, c) passing over $CO_2$ at temperatures between $-25°$ and $+15°$ C., d) addition of sulfuric acid for neutralization and dehydration, e) separating the phases and concentrating under reduced pressure, f) dissolving the residue in a hydrocarbon as a solvent and washing the organic phases with aqueous alkali, g) acidifying the aqueous phase with a mineral acid and extraction of the aqueous phase with a hydrocarbon, h) concentrating the organic phase of g) under reduced pressure.

Preferred embodiments of the process according to the invention are:

a) Processes where step a) is carried out at temperatures between $40°$ and $70°$ C.

b) Processes where, in step a), 1.6 to 2.2 mol of magnesium, 0.005 to 0.020 mol of 1,2-dibromoethane, and a total of 1.5 to 2.2 kg of tetrahydrofuran are employed relative to 1 mol of 1,4-dichlorobutane.

c) Processes where, in step b), 0.6 to 1.0 mol of thiolactone of the formula II dissolved in 0.8 to 1.2 kg of tetrahydrofuran are used, relative to 1 mol of 1,4-dichlorobutane employed in step a).

d) Processes where, in step b), subsequent stirring is carried out under reduced pressure, preferably between 0.1 and 0.3 bar.

e) Processes where step c) is carried out at a pressure between 0.5 and 1.0 bar, in particular where the carbon dioxide is passed over in the course of 15 to 45 minutes, and/or where the mixture obtained after passing over the carbon dioxide is warmed to temperatures between 30° and 60° C. with pressure equalization.

f) Processes where step d) is carried out at temperatures between 45° and 70° C.

g) Processes where step e) is carried out at temperatures between 30° and 55° C.

h) Processes where, in step f), an aromatic hydrocarbon is selected and the organic phase is washed with an aqueous alkali which has a pH between 8.0 and 9.5, preferably between 8.4 and 9.1.

The invention further relates to the use of compounds of the formula I, prepared by the process according to the invention, for the preparation of D-(+)-biotin in a manner known per se.

The compound of the formula II used as starting material, and also the compound of the formula I prepared according to the invention are known compounds (e.g. EP 0 084 377 R=benzyl or EP 0 273 270 R=1-phenylethyl).

The compound of the formula I obtained after dehydration is, as already mentioned, a known compound (e.g. EP offenlegungsschrift 084 377) and can easily be converted into D-(+)-biotin in a known manner, i.e. by hydrogenation of the double bond and removal of the protective groups on the nitrogen atoms (e.g. CH Patent Specification 556867).

The following examples illustrate the invention.

EXAMPLE 1

Preparation of cis-2-oxo-1,3-dibenzyl-4-(4-carboxybutyl-1-idene)hexahydro-1H-thieno[3,4-d]imidazole Under nitrogen, 41.5 g (1.69 mol) of magnesium turnings are initially introduced into 489.5 g of THF and the mixture is heated to boiling. A solution of 117.0 g (0.91 mol) of dichlorobutane in 1246.0 g of THF and also 1.23 g (0.0065 mol) of dibromoethane are added to this suspension in the course of approximately 1 hour. The reaction mixture is heated to boiling for 45 minutes and subsequently stirred at room temperature for 16 hours.

It is then cooled to −15° C. A solution of 222.2 g (0.65 mol) of (+)-cis-1,3-dibenzylhexahydro-1H-thieno-[3,4-d] imidazole-2,4-dione in 867.8 g of THF is added dropwise in the course of 95 minutes at a temperature between −14° and −16° C.

After stirring for 10 minutes, the reaction vessel is evacuated in the course of 5 minutes at a pressure of 0.2 bar.

Carbon dioxide is passed over for 15 minutes at a temperature of −20° C. and a pressure of 0.6 bar, the temperature slowly rising to 0° C.

With further passing-over of carbon dioxide at temperatures up to 15° C., the pressure stabilizes at 0.9 bar.

The reaction mixture is warmed to +50° C. with pressure equalization in the course of 40 minutes.

1000 g of 30% sulfuric acid are then added in the following manner:

150 ml of sulfuric acid are added in the course of 10. minutes, the temperature rising to 60°–62° C.

The remaining sulfuric acid is added in the course of 15 minutes, the temperature falling to 52° C. The reaction mixture is then kept at temperatures between 52° and 56° C. and stirred for 70 minutes. The phases are separated at this temperature and the organic phase is concentrated in vacuo. The residue is taken up in 650 ml of toluene, the remaining sulfuric acid is separated off and the organic phase is washed with 250 ml of water.

The organic phase is then treated with 715 ml of 1 molar sodium hydroxide solution. After separating the phases, the aqueous phase is extracted two times with 250 ml of toluene. The organic phases are combined and evaporated in vacuo. The aqueous phase is treated with 650 ml of toluene and adjusted to pH 6.5 with 45 ml of concentrated hydrochloric acid. The organic phase is separated off and evaporated in vacuo. 228.3 g (83.1% of theory) of the desired product are obtained in the form of white needles having a melting point of 80°–83.5° C.

Starting from 0.5 mol of (+)-cis-1,3-di-(1-phenylethyl) hexahydro-1H-thieno[3,4-d]imidazole(-2,4-dione), 164.9 g (73.2% of theory) of cis-2-oxo-1,3-di-(1-phenylethyl)-4-(4-carboxybutyl-1-idene)hexahydro-1H-thieno[3,4-d] imidazole are obtained analogously as a yellowish oil.

We claim:

1. An improved process for the preparation of a D-(+)-biotin intermediate of the formula I

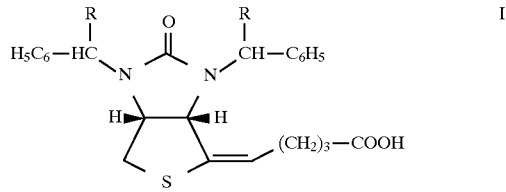

in which

R is H or $C_{1-6}$-alkyl, by reacting a thiolactone of the formula II

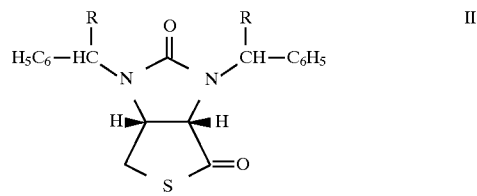

in which R has the meaning indicated, with 1,4-dimagnesiumchlorobutane and carbon dioxide in an inert solvent and subsequently eliminating water using a mineral acid, wherein the following steps are carried out successively:

a) reacting 1,4-dichlorobutane with magnesium turnings in the presence of catalytic amounts of 1,2-dibromoethane in tetrahydrofuran as a solvent, b) adding thereto the thiolactone of the formula II, dissolved in tetrahydrofuran at temperatures between −25° and −15° C., and, if appropriate, subsequently stirring, c) passing over $CO_2$ at temperatures between −25° and −15° C., d) adding sulfuric acid for neutralization and dehydration, e) separating the phases and concentrating under reduced pressure, f) dissolving the residue in a hydrocarbon solvent and washing the organic phases with aqueous alkali, g) acidifying the aqueous phase with a mineral acid and extracting the aqueous phase with a hydrocarbon, and h) concentrating the organic phase remaining from g) under reduced pressure.

2. Process according to claim 1, wherein step a) is carried out at temperatures between 40° and 70° C.

3. Process according to claim 1, wherein, in step a), 1.6 to 2.2 mol of magnesium, 0.005 to 0.020 mol of 1,2-dibromoethane, and a total of 1.5 to 2.2 kg of tetrahydrofuran are employed relative to 1 mol of 1,4-dichlorobutane.

4. Process according to claim 1, wherein, in step b), 0.6 to 1.0 mol of thiolactone of the formula II dissolved in 0.8 to 1.2 kg of tetrahydrofuran are used, relative to 1 mol of 1,4-di-chlorobutane employed in step a).

5. Process according to claim 1, wherein, in step b), subsequent stirring is carried out under reduced pressure.

6. Process according to claim 1, wherein, step c) is carried out at a pressure between 0.5 and 1.0 bar.

7. Process according to claim 6, wherein the carbon dioxide is passed over in the course of 15 to 45 minutes.

8. Process according to claim 6, wherein the mixture obtained after passing over the carbon dioxide is warmed to temperatures between 30° and 60° C. with pressure equalization.

9. Process according to claim 1, wherein step d) is carried out at temperatures between 45° and 70° C.

10. Process according to claim 1, wherein step e) is carried out at temperatures between 30° and 55° C.

11. Process according to claim 1, wherein, in step f), an aromatic hydrocarbon is selected and the organic phase is washed with an aqueous alkali which has a pH between 8.0 and 9.5.

12. A process for the preparation of D-(+)-biotin which comprises preparing a D-(+)-biotin intermediate according the process of claim 1 and preparing D-(+)-biotin from such intermediate.

13. The process of claim 5, wherein the subsequent stirring is carried out under a pressure between 0.1 and 0.3 bar.

14. The process of claim 11, wherein the aqueous alkali has a pH between 8.4 and 9.1.

* * * * *